(12) United States Patent
Miz et al.

(10) Patent No.: US 12,714,471 B2
(45) Date of Patent: Aug. 25, 2026

(54) PARS CLAMP

(71) Applicant: K2M, Inc., Leesburg, VA (US)

(72) Inventors: George Miz, Chicago, IL (US); Larry E. McClintock, Gore, VA (US)

(73) Assignee: VB Spine US Opco LLC, Leesburg, VA (US)

( * ) Notice: Subject to any disclaimer, the term of this patent is extended or adjusted under 35 U.S.C. 154(b) by 702 days.

(21) Appl. No.: 17/954,779

(22) Filed: Sep. 28, 2022

(65) Prior Publication Data

US 2023/0107405 A1 Apr. 6, 2023

Related U.S. Application Data

(60) Provisional application No. 63/252,825, filed on Oct. 6, 2021.

(51) Int. Cl.
*A61B 17/70* (2006.01)

(52) U.S. Cl.
CPC ...... *A61B 17/7037* (2013.01); *A61B 17/7032* (2013.01); *A61B 17/704* (2013.01); *A61B 17/7082* (2013.01)

(58) Field of Classification Search
CPC ............ A61B 17/7032; A61B 17/7037; A61B 17/704; A61B 17/7049–7052; A61B 17/7056; A61B 17/7067; A61B 17/7082
See application file for complete search history.

(56) References Cited

U.S. PATENT DOCUMENTS 5,102,412 A * 4/1992 Rogozinski ........ A61B 17/7082 606/267
5,281,223 A * 1/1994 Ray .................... A61B 17/7079 606/86 R
5,312,410 A 5/1994 Miller et al.
5,383,392 A 1/1995 Kowalewski et al.
5,437,669 A * 8/1995 Yuan .................. A61B 17/7047 606/264

(Continued)

FOREIGN PATENT DOCUMENTS

EP 0649636 A2 4/1995
EP 2052689 A1 4/2009

(Continued)

OTHER PUBLICATIONS

International Search Report for Application No. PCT/US2017/056099 dated Jan. 8, 2018, 2 pages.

(Continued)

*Primary Examiner* — Nicholas J Plionis
(74) *Attorney, Agent, or Firm* — Lerner David LLP

(57) ABSTRACT

A clamp device includes multiple claws for collectively gripping a vertebra, particularly over a pars interarticularis. At least one of the claws is movable relative to a body of the clamp device. The movable claw includes an elongate tab received within a track extending within the body. The body or the tab includes a threaded hole within which set screws may be received for immobilizing the movable claw relative to the body. The clamp device also includes an array of rod clamps. The rod clamps are supported by the body, and more directly by a bar supported by the body. The bar is releasably connectable to the body, and the rod clamps are pivotably connectable to the bar.

10 Claims, 11 Drawing Sheets

(56) References Cited

U.S. PATENT DOCUMENTS 5,439,463 A * 8/1995 Lin .................... A61B 17/7052 606/252
5,449,361 A 9/1995 Preissman
5,496,318 A 3/1996 Howland et al.
5,683,392 A 11/1997 Richelsoph et al.
5,702,392 A * 12/1997 Wu .................... A61B 17/7043 606/264
5,702,452 A * 12/1997 Argenson ........... A61B 17/7049 606/253
5,707,372 A 1/1998 Errico et al.
5,733,286 A 3/1998 Errico et al.
5,941,881 A * 8/1999 Barnes ............... A61B 17/8004 606/74
6,086,590 A 7/2000 Margulies et al.
6,136,000 A * 10/2000 Louis ................ A61B 17/7047 606/279
6,238,396 B1 5/2001 Lombardo
6,436,099 B1 8/2002 Drewry et al.
6,589,243 B1 7/2003 Viart et al.
7,285,121 B2 10/2007 Braun et al.
7,344,539 B2 3/2008 Serhan et al.
7,481,828 B2 1/2009 Mazda et al.
7,658,582 B2 2/2010 Doubler et al.
7,717,940 B2 5/2010 Woods et al.
7,771,430 B2 8/2010 Jones et al.
7,862,590 B2 1/2011 Lim et al.
7,909,826 B2 3/2011 Serhan et al.
7,959,654 B2 6/2011 Mazda et al.
7,988,694 B2 8/2011 Barrus et al.
RE42,867 E 10/2011 Hammill, Sr. et al.
8,029,513 B2 10/2011 Konno et al.
8,113,847 B2 2/2012 Boachie-Adjei
8,162,946 B2 4/2012 Baccelli et al.
8,162,991 B2 4/2012 Strauss et al.
8,167,915 B2 5/2012 Ferree et al.
8,172,843 B2 5/2012 Baccelli et al.
8,287,576 B2 10/2012 Barrus
8,308,729 B2 11/2012 Nunley et al.
8,308,771 B2 11/2012 Bennett et al.
8,323,294 B2 12/2012 Mickiewicz et al.
8,337,532 B1 12/2012 McLean et al.
8,361,122 B2 1/2013 Barrus et al.
8,372,120 B2 * 2/2013 James ................ A61B 17/7052 606/250
8,377,104 B2 2/2013 Jones et al.
8,403,971 B2 3/2013 Barrus et al.
8,465,495 B2 6/2013 Belliard
8,486,110 B2 7/2013 Fielding et al.
8,506,603 B2 8/2013 McClintock et al.
8,672,944 B2 3/2014 Boachie-Adjei et al.
8,696,718 B2 4/2014 Barrus et al.
8,714,427 B2 5/2014 McClintock et al.
8,728,083 B2 5/2014 Baccelli et al.
8,764,756 B2 7/2014 Jones
8,814,919 B2 8/2014 Barrus et al.
8,834,474 B2 9/2014 Jones et al.
8,882,817 B2 11/2014 Jones et al.
8,926,668 B2 1/2015 Douget
8,936,625 B2 1/2015 Larroque-Lahitette et al.
8,945,189 B2 2/2015 Barrus et al.
8,961,523 B2 2/2015 Barrus et al.
8,979,898 B2 3/2015 Ark et al.
9,023,087 B2 5/2015 Frankel et al.
9,125,703 B2 9/2015 McClintock et al.
9,173,685 B2 11/2015 Lindquist et al.
9,247,969 B2 2/2016 Nunley et al.
9,314,275 B2 4/2016 Clement et al.
9,381,044 B2 * 7/2016 Robinson ........... A61B 17/7052
9,393,049 B2 7/2016 Jones et al.
9,675,386 B2 6/2017 Akbarnia et al.
9,770,267 B2 9/2017 Lindquist et al.
9,770,268 B2 9/2017 Albert et al.
10,064,656 B2 9/2018 Mundis, Jr. et al.
10,198,970 B2 2/2019 McClintock et al.
10,307,186 B2 6/2019 Schafer et al.
10,610,265 B1 4/2020 Ark et al.
10,667,852 B2 6/2020 Shoshtaev
10,918,419 B2 2/2021 Kishan et al.
11,213,325 B2 * 1/2022 Donner .............. A61B 17/7071
2002/0007183 A1 1/2002 Lee et al.
2002/0052603 A1 * 5/2002 Nichols .............. A61B 17/7052 606/250
2002/0116013 A1 8/2002 Gleason et al.
2002/0143330 A1 10/2002 Shluzas
2003/0187435 A1 * 10/2003 Lin .................... A61B 17/7001 606/252
2005/0228375 A1 10/2005 Mazda
2005/0277920 A1 12/2005 Slivka et al.
2006/0217710 A1 * 9/2006 Abdou ............... A61B 17/6433 606/54
2006/0241591 A1 * 10/2006 Biscup ............... A61B 17/7047 606/60
2006/0241598 A1 10/2006 Khalili
2006/0241601 A1 * 10/2006 Trautwein .......... A61B 17/7067 606/279
2007/0016189 A1 1/2007 Lake et al.
2007/0016197 A1 1/2007 Woods et al.
2008/0015588 A1 1/2008 Hawkes
2008/0021454 A1 * 1/2008 Chao .................. A61B 17/7044 606/250
2008/0086134 A1 4/2008 Butler et al.
2008/0109039 A1 * 5/2008 Michielli ........... A61B 17/7049 606/246
2008/0177323 A1 7/2008 Null et al.
2008/0281361 A1 * 11/2008 Vittur ................. A61B 17/7052 606/100
2008/0306538 A1 * 12/2008 Moore ............... A61B 17/7052 606/250
2009/0149885 A1 * 6/2009 Durward ........... A61B 17/7067 606/279
2009/0204118 A1 8/2009 Pratt
2009/0292308 A1 11/2009 Jones et al.
2009/0292317 A1 11/2009 Belliard
2009/0326585 A1 12/2009 Baccelli
2010/0114171 A1 * 5/2010 Boachie-Adjei ... A61B 17/7008 606/264
2010/0185243 A1 7/2010 Pasquet et al.
2011/0106185 A1 5/2011 Gil et al.
2011/0137345 A1 * 6/2011 Stoll .................. A61B 17/7067 606/279
2011/0152934 A1 6/2011 Asaad
2011/0238118 A1 9/2011 Baccelli et al.
2011/0245871 A1 * 10/2011 Williams ........... A61B 17/8863 606/250
2011/0301644 A1 12/2011 Belliard
2012/0035659 A1 2/2012 Barrus et al.
2012/0130373 A1 5/2012 Larroque-Lahitette
2012/0226316 A1 9/2012 Dant et al.
2012/0271356 A1 10/2012 Ramsay et al.
2013/0041410 A1 2/2013 Hestad et al.
2013/0053888 A1 * 2/2013 Torres ................ A61B 17/7052 606/252
2014/0094850 A1 4/2014 Clement et al.
2014/0257397 A1 9/2014 Akbarnia et al.
2014/0277142 A1 9/2014 Blain et al.
2014/0316468 A1 10/2014 Keiser et al.
2014/0343612 A1 11/2014 Rezach et al.
2015/0032158 A1 * 1/2015 Khajavi ................. A61B 50/30 606/246
2015/0320448 A1 11/2015 Legallois
2016/0058478 A1 3/2016 Agarwal et al.
2016/0157896 A1 6/2016 Palmer et al.
2017/0265901 A1 * 9/2017 Hawkins ............ A61B 17/8023
2017/0303970 A1 10/2017 Puryear et al.
2017/0348025 A1 12/2017 Albert et al.
2018/0008321 A1 * 1/2018 Stern .................. A61B 17/7043
2018/0368889 A1 12/2018 Cole
2020/0100816 A1 * 4/2020 Mundis, Jr. ........ A61B 17/8869
2020/0289167 A1 * 9/2020 Miz .................... A61B 17/7052

(56) References Cited

U.S. PATENT DOCUMENTS

| | | | | |
|---|---|---|---|---|
| 2020/0337750 | A1* | 10/2020 | Hu | A61B 17/7056 |
| 2021/0052306 | A1* | 2/2021 | Ebara | A61B 17/7047 |

FOREIGN PATENT DOCUMENTS

| | | | |
|---|---|---|---|
| EP | 2279707 | A1 | 2/2011 |
| EP | 2316363 | A1 | 5/2011 |
| FR | 2849590 | A1 | 7/2004 |
| WO | 2012176096 | A1 | 12/2012 |
| WO | 2013001180 | A1 | 1/2013 |
| WO | 2021226057 | A1 | 11/2021 |

OTHER PUBLICATIONS

European Search Report for Application No. 17860758.6, dated May 19, 2020, 9 pages.
European Office Action dated Oct. 15, 2018 cited in EP Application 14 158 813.
European Search Report dated Jun. 18, 2014 issued in European U.S. Appl. No. 14/158,813.
Australian Examination Report dated Jul. 10, 2017, issued in AU Application No. 2014201336.
Australian Office Action dated Dec. 15, 2017, issued in AU Application No. 2014201336.

* cited by examiner 37
37
36
16
36
44
38
38
52
25
24
52

PARS CLAMP

CROSS-REFERENCE TO RELATED APPLICATIONS

This application claims the benefit of the filing date of U.S. Provisional Patent Application No. 63/252,825 filed Oct. 6, 2021, the disclosure of which is hereby incorporated herein by reference.

BACKGROUND

The spine is a flexible structure capable of a large range of motion. There are various disorders, diseases and types of injury, which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages and cadaver and human bone implants. In order to facilitate stabilizing the spine and keeping the interbody in position, other implants are commonly employed, such as bone screws and spinal rods.

Securing the spinal rods using bone screws on a vertebra that may be too small, too fragile, or damaged to secure a bone screw thereon may be problematic. Furthermore, the use of bone screws also requires a substantial amount of work, time, and hardware during a surgical procedure.

Therefore, a continuing need exists for an improved device and a methods for securing spinal rods to bone.

BRIEF SUMMARY

According to some aspects, a clamp device may include multiple claws for collectively gripping a vertebra, particularly over a pars interarticularis. At least one of the claws may be movable relative to a body of the clamp device, while a remainder of the claws may be either movable or immovable relative to the body. The immovable claws may be connected to or integrally formed with the body. The movable claws may include elongate tabs received within tracks extending within the body. The body or the tabs may include threaded holes within which set screws may be received for immobilizing the movable claws relative to the body.

The clamp device may include an array of rod clamps. The rod clamps may be supported by the body, and may more directly be supported on a bar supported by the body. The bar may be releasably connectable to the body. The rod clamps may be pivotably connectable to the bar.

The foregoing components may be part of a modular kit. The kit may include multiple interchangeable claws of different sizes. The kit also may include bars of different sizes.

According to another aspect, a clamp device for securing at least one spinal rod to a vertebra may comprise a body, an array of rod clamps supported by the body for releasably retaining a spinal rod, a first claw that is movably connected to the body, and a second claw that is either connected to the body or integrally formed with the body.

In another arrangement according to any of the foregoing, the array of rod clamps may be releasably secured to the body.

In another arrangement according to any of the foregoing the array of rod clamps may be supported by a bar that is releasably connected to the body and to which each rod clamp is pivotably connected.

In another arrangement according to any of the foregoing, each rod clamp in the array of rod clamps may be connected to the bar by a ball and socket joint.

In another arrangement according to any of the foregoing, the body may include a tulip provided by opposed walls between which the bar is retained.

In another arrangement according to any of the foregoing, the clamp device may comprise a third claw that is movably connected to the body and wherein the first claw and third claw are removable from the body.

In another arrangement according to any of the foregoing, third claw may be different in size than the first claw and the second claw.

In another arrangement according to any of the foregoing, the first claw may include a hook and an elongated tab extending from an end of the hook, and the body may include a track within which the tab is received.

In another arrangement according to any of the foregoing, the tab may include a threaded hole extending therethrough, and the clamp device includes a set screw that may be driven through the hole to bear on a surface of the track.

In another arrangement according to any of the foregoing, the body may include a threaded hole extending through a portion of the body to open into the track and the clamp device includes a set screw that may be driven through the hole to extend into the track.

In another arrangement according to any of the foregoing, the tab and the track may dovetail together or create a dovetail connection to one another when the tab is received in the track.

In another arrangement according to any of the foregoing, the track may be a first track, and the body may include two wings extending generally away from one another. The first track may extend within and along one of the wings, and a second track may also receive the tab may extend within and along another one of the wings.

In another arrangement according to any of the foregoing, a third track that may also receive the tab may extend within the body at a location centered between the wings.

In another arrangement according to any of the foregoing, each rod clamp in the array of rod clamps may include two jaws that meet at a living hinge provided by notches extending into the rod clamp from opposite sides of the rod clamp.

In another arrangement according to any of the foregoing, the clamp device may comprise a lag screw for each rod clamp in the array of rod clamps that includes a threaded portion and a head of larger diameter than the threaded portion at an opposite end of the lag screw from the threaded potion. Each rod clamp in the array of rod clamps may include a bore and threads within the bore for threadingly engaging the threaded portion of the lag screw. The bore may extend across the living hinge and have both an open end and a portion too small in diameter to accept the head of the lag screw on an opposite side of the living hinge from the threads of the rod clamp.

In another aspect, a kit for securing a spinal rod to a vertebra may comprise a body within which a plurality of elongate tracks extend, a first claw and a second claw of a different size than the first claw, the first claw and the second claw each including an elongate tab slidingly receivable within any one of the tracks, and a rod clamp releasably connectable to the body.

In another arrangement according to any of the foregoing, the kit may comprise a plurality of bars of differing lengths releasably connectable to the body and to which the rod clamp may be connected.

In another arrangement according to any of the foregoing, the body may include two opposed walls defining a tulip within which any of the plurality of bars may be releasably fixed.

In another arrangement according to any of the foregoing, the plurality of elongate tracks may be at least three elongate tracks.

In another arrangement according to any of the foregoing, the body is a first body and the plurality of tracks is a first plurality of tracks and further comprising a second body including a second body that includes a second plurality of tracks in which the elongate tabs are slidingly receivable, the second plurality of tracks including a different number of tracks than the first plurality of tracks.

In another aspect, a method of coupling a spinal rod to a vertebra may comprise placing a clamp device including two claws over a pars interarticularis of the vertebra, moving at least one of the claws relative to a body of the clamp device such that the claws collectively grip the vertebra, and clamping a spinal rod with a rod clamp supported by the body.

In another arrangement according to any of the foregoing, the method may comprise, before the moving step, selecting at least one of the claws for use from within a kit including a plurality of claws of different sizes.

In another arrangement according to any of the foregoing, the method may further comprise, after the placing step but before the clamping step, selecting a bar from a plurality of bars within a kit including a plurality of bars of different lengths to which the rod clamps of the rod clamp array are or may be connected and fixing the selected bar to the body.

In another arrangement according to any of the foregoing, the method may further comprise, before the placing step, selecting the body from a kit including a plurality of bodies including differing arrangements of tracks within which elongate tabs of the claws may be slidingly received, and assembling the claws with the selected body.

In another arrangement according to any of the foregoing, the method may further comprise, before the moving step, bending the body to alter an angle at which a track within which a portion of a claw is received during the moving step relative to a remainder of the body.

BRIEF DESCRIPTION OF THE DRAWINGS

FIG. 5B is a front elevation view of the clamp device fixed to the vertebra of FIG. 5A.

FIG. 5C is a side elevation view of the clamp device fixed to the vertebra of FIG. 5A.

DETAILED DESCRIPTION

The terms "cephalad" or "superior" are used in this application to indicate a direction towards a patient's head, whereas the terms "caudad," "caudal," or "inferior" indicate a direction towards the patient's feet. The term "medial" indicates a direction towards the middle of the body of the patient, while the term "lateral" indicates a direction towards a side of the body of the patient (i.e., left or right away from the middle of the patient's body). The term "posterior" indicates a direction towards the patient's back, and the term "anterior" indicates a direction towards the patient's front.

Figure 1A:
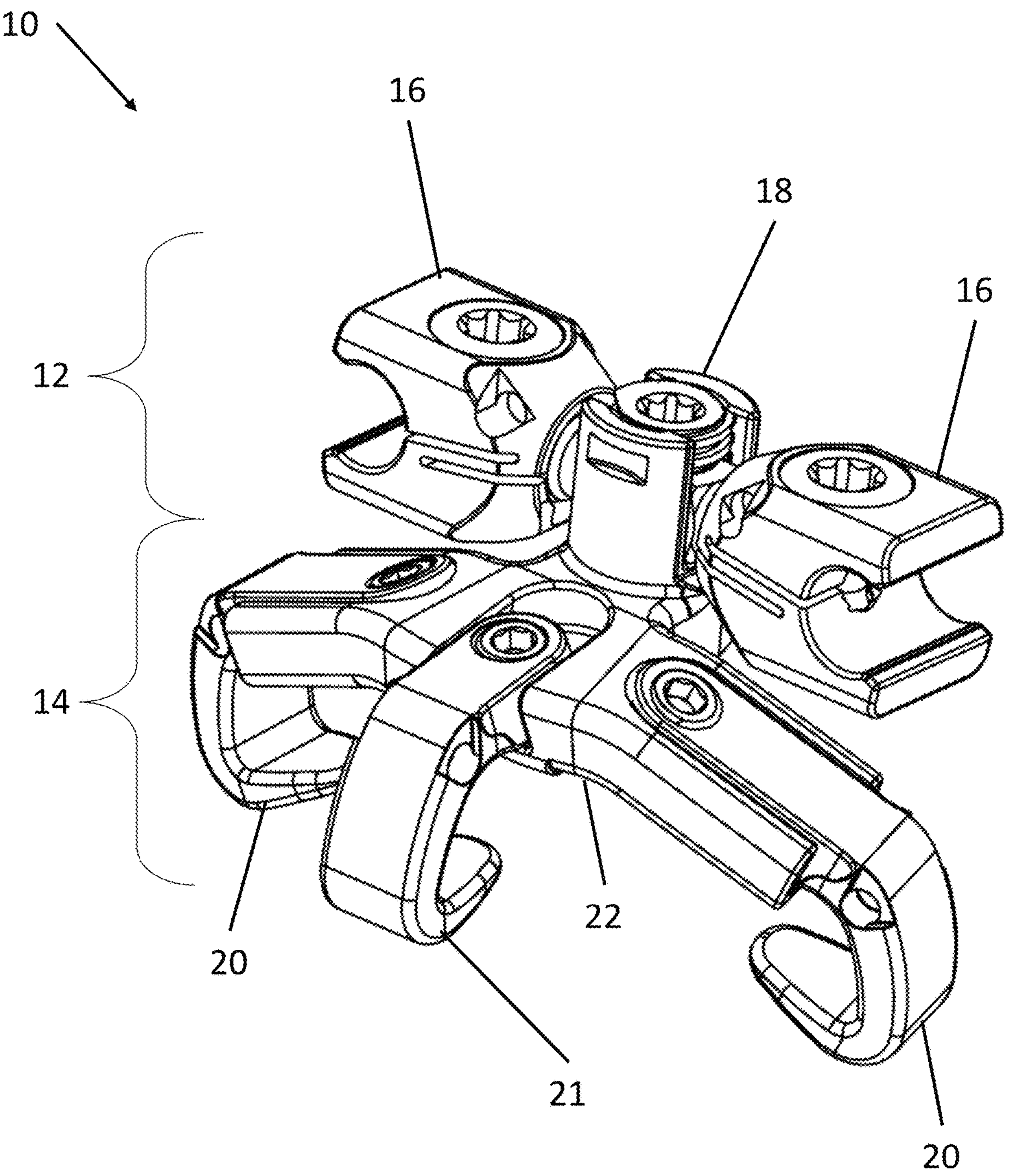
FIG. 1A is an oblique perspective view of a clamp device.
Figure 1B:
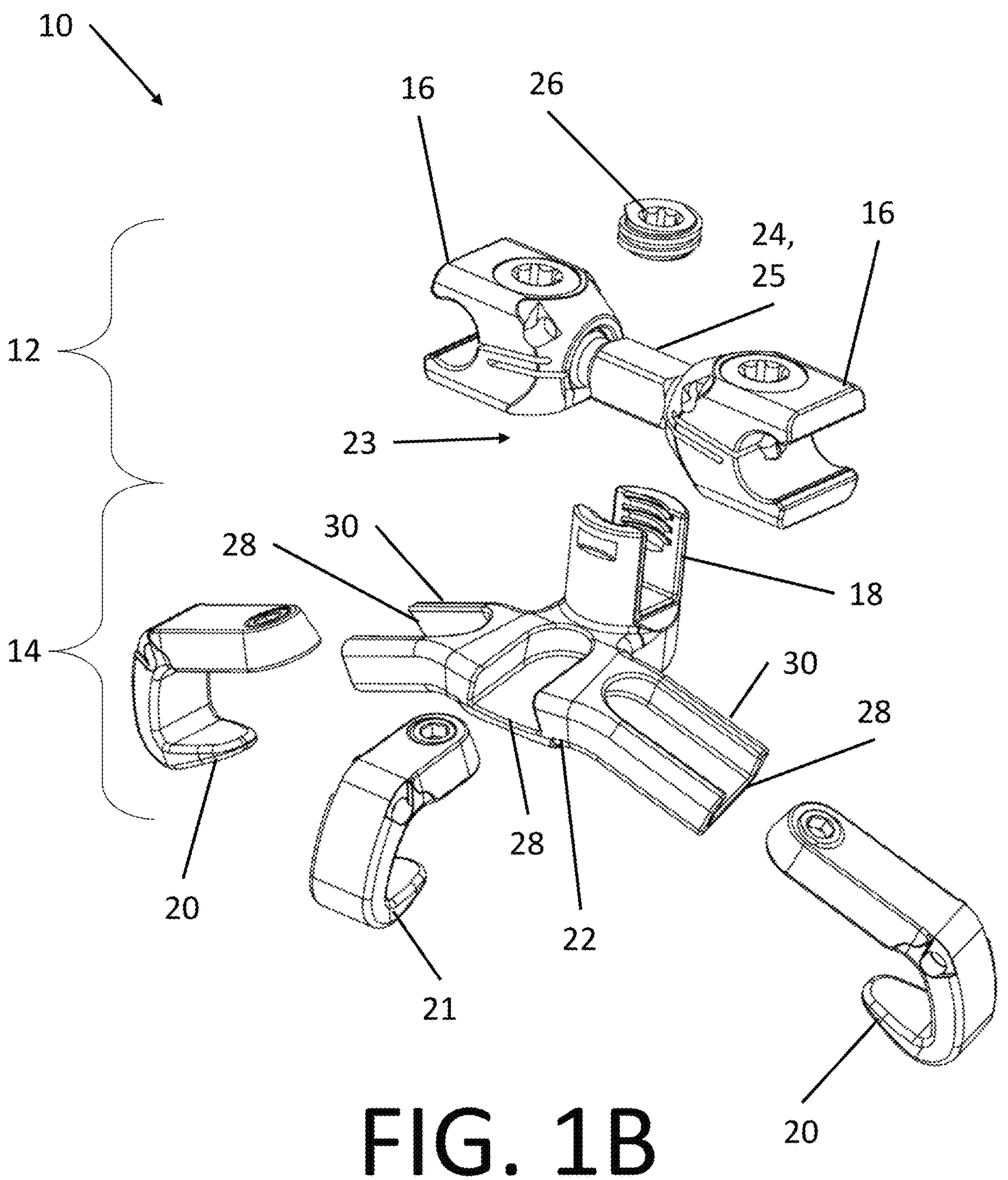
FIG. 1B is an exploded illustration of the clamp device of FIG. 1A.

Referring now to FIGS. 1A and 1B, a clamp device 10 includes a rod clamping portion 12 and a pars clamping portion 14. Having respective portions for clamping to spinal rods and a pars interarticularis enables clamping device 10 to couple a vertebra to spinal correction rods. In particular, clamping device 10 according to the illustrated arrangement is able to couple the rods to a vertebra without the use of fasteners and with relatively little removal or destruction of bone, though fasteners may be used to reinforce the connection between a vertebra and clamping devices according to other examples.

In the illustrated arrangement, rod clamping portion 12 includes two adjustably positionable rod clamps 16. Rod clamps 16 are part of a rod clamp array 23 including a dumbbell 25. A bar 24 of dumbbell 25 is visible in FIG. 1B. Bar 24 is retainable within a tulip 18 of clamp device 10 by a set screw 26. Rod clamping portion 12 of other arrangements may be structured differently, such as by including more or fewer rod clamps 16 or rod clamps that are either or both of non-adjustably positioned or non-removable from clamping device 10. Rod clamp array 23 is shown in more detail in FIG. 3A, and discussed more fully below.

Further according to the illustrated arrangement, pars clamping portion 14 includes multiple adjustably positionable claws 20, 21. Each claw 20, 21 is slidably postionable in a respective track 28 in a body 22 of clamp device 10. After body 22 is appropriately positioned over a target pars interarticularis, claws 20, 21 may therefore be repositioned to hook tightly around portions of the pars interarticularis to prevent movement of the body relative to the corresponding vertebra. Because claws 20, 21 are removable from tracks 28, any one of the claws of the illustrated example may be omitted if only two claws would be needed to satisfactorily immobilize body 22 relative to the vertebra. Further, claws of different shapes and sizes may be chosen for any of tracks 28 as appropriate for a given procedure and anatomical structure. Accordingly, the shapes and proportions of claws 20, 21 of the illustrated arrangement are merely examples, and clamp device 10 may be provided in a modular kit including claws such as claws 20, 21 in a variety of shapes and sizes. Pars clamping portion 14 of other arrangements may also be structured differently, such as by including claws that are immovable relative to or irremovable from body 22 or by including claws in any quantity of two or greater. Pars clamping portions 14 according to some arrangements may have at least one immovable claw and one or more tracks 28 extending at any angle relative to the immovable claw.

FIGS. 2A-2D illustrate additional features of body 22 of the illustrated arrangement. Additional features described here with regard to FIGS. 2A-2D are example of a structure that facilitates the above described aspects of rod clamping portion 12 and pars clamping portion 14, but the above described aspects of the clamping portions could be implemented with different structures than the illustrated example. Moreover, it is contemplated that body 22 could be designed such that bending or other manipulation is permitted. This could allow the surgeon to tailor the body to a given patient prior to or during the surgical procedure.

Body 22 includes tulip 18, which is provided by two spaced apart, arcuate walls 34. Each wall 34 includes internal threading on a surface facing the opposite wall. The internal threading, spacing, and arcuate shapes of walls 34 are collectively configured such that a circular set screw 26 may be threaded between the walls to trap bar 24 between the set screw and a floor 32 defining the bottom of tulip, thereby immobilizing dumbbell 25 relative to body 22. Indeed, tulip 18 is similar in many respects to a typical pedicle screw coupling element.

Body 22 also includes two wings 30 extending in nearly opposite lateral directions. One track 28 extends along each wing 30, and a third track 28 is centered between the wings. In the illustrated arrangement, from the top-down perspective of FIG. 2C, wings 30 define a concave angle on a side on which tulip 34 is located, and a convex angle at the opening of the track 28 that is centered between the wings. Further according to the illustrated arrangement, the concave angle between wings 30 is 70°, and the convex angle between the wings is 110°. However, in various other arrangements, these angles may vary, tulip 34 may be located on the convex side, a track 28 may open also or only on the concave side, or wings 30 may extend parallel to one another. Yet further according to the illustrated arrangement, tracks 28 extending along wings 30 are longer than the third track centered between the wings, but the relative lengths of the tracks may differ in other arrangements. It is also contemplated that the various angles can be manipulated via a bending procedure or the like to tailor the assembly to a given patient.

Figure 2A:
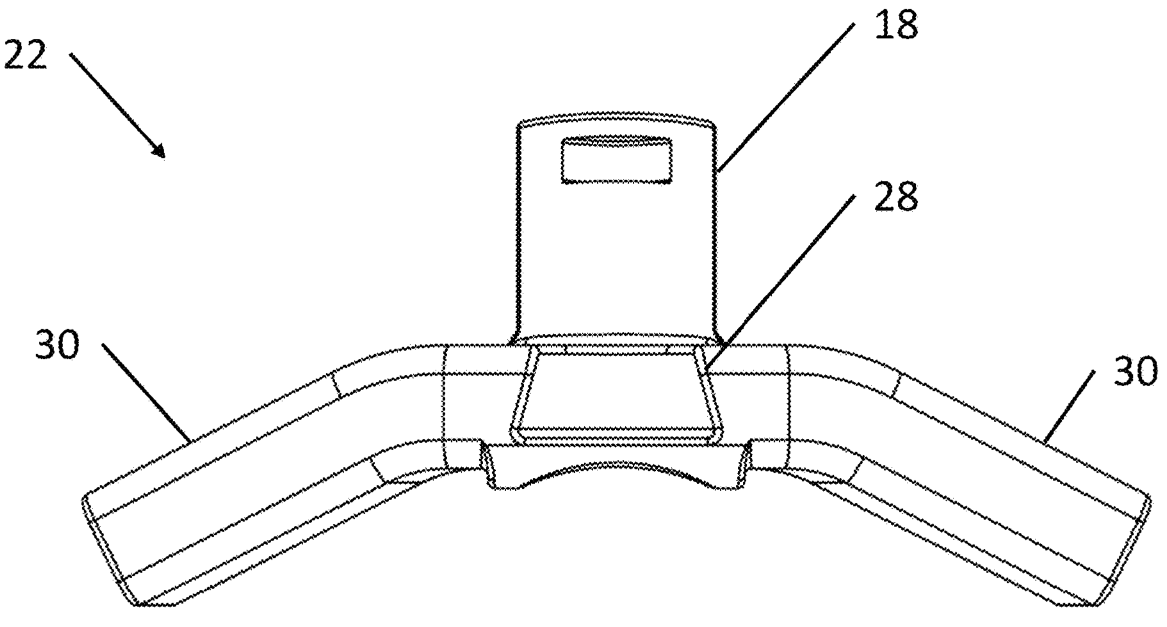
FIG. 2A is a front elevation view of a body of the clamp of FIG. 1A.
Figure 2B:
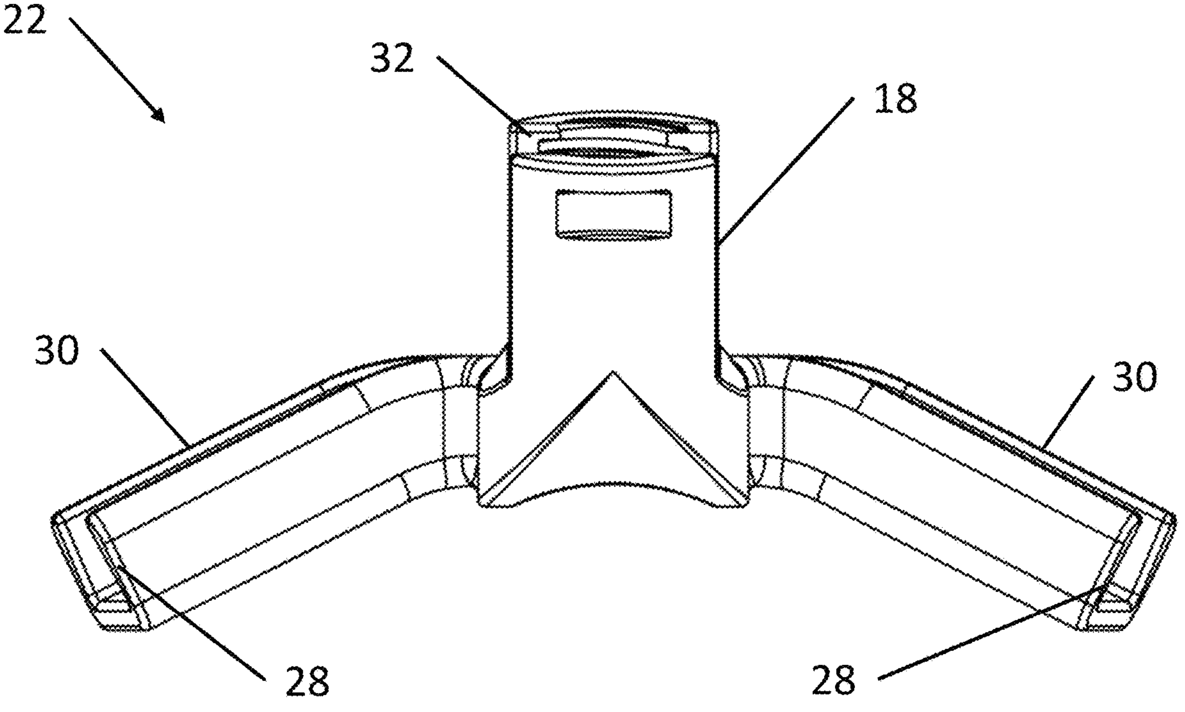
FIG. 2B is a back elevation view of the body of FIG. 2A.
Figure 2C:
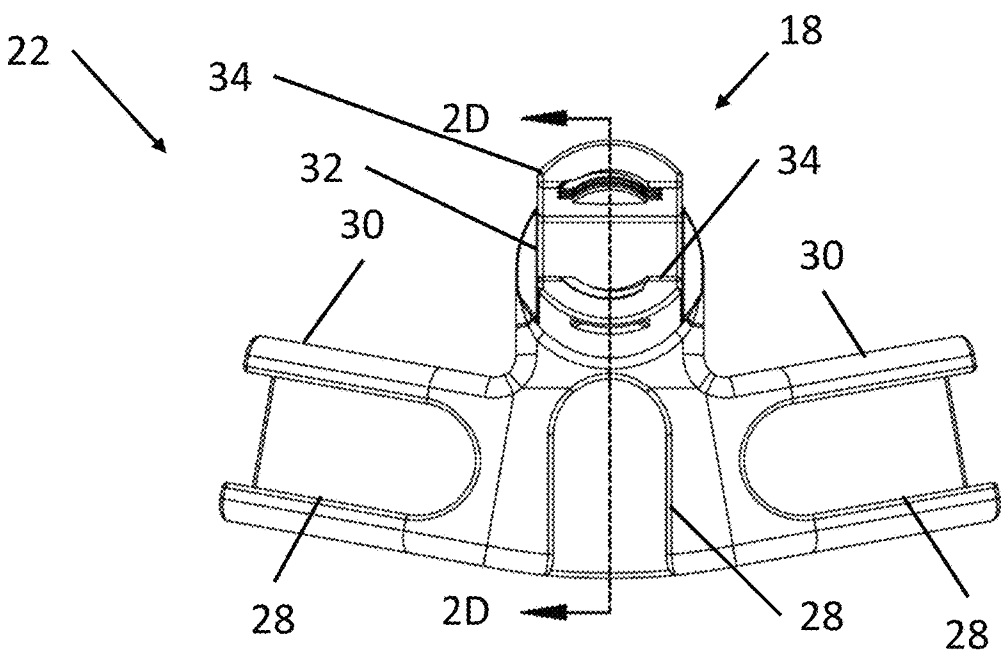
FIG. 2C is a top plan view of the body of FIG. 2A.
Figure 2D:
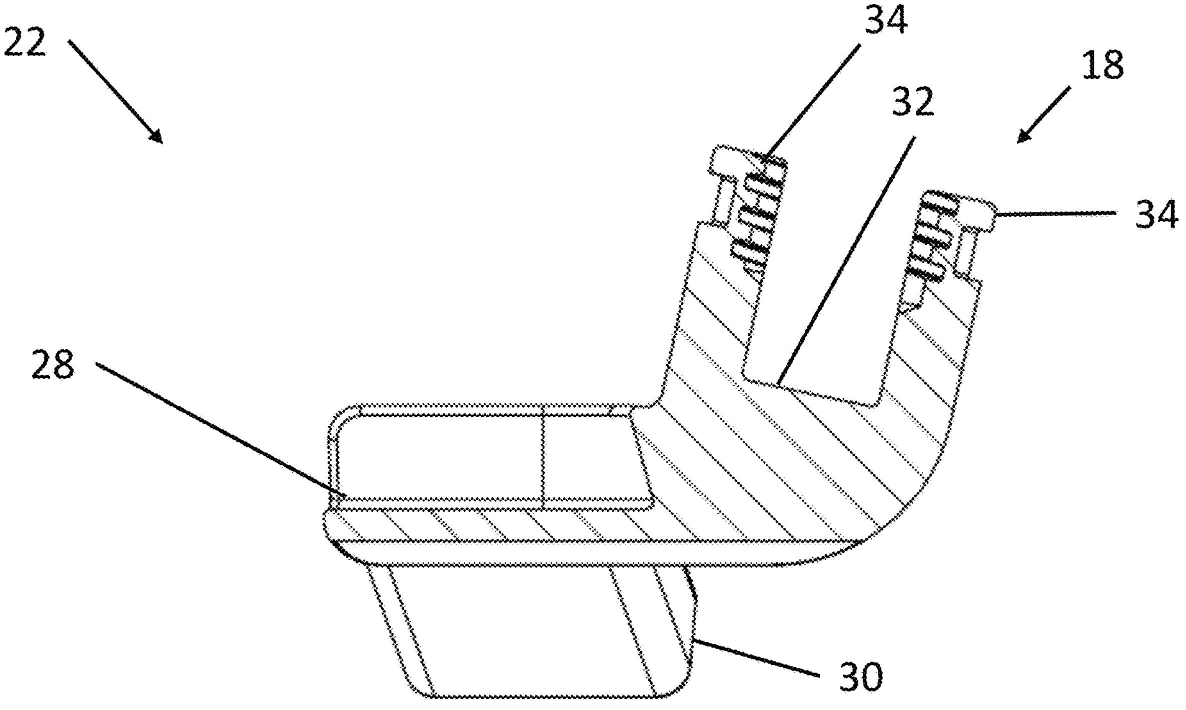
FIG. 2D is a view along section 2D-2D of FIG. 2C.

Tracks 28 each have a trapezoidal or dovetail cross-sectional shape visible at their open ends, such as shown on the centered track in FIG. 2A. Tracks 28 are only open on the narrower side of the trapezoidal shape. Thus, when a correspondingly shaped portion of a claw 20, 21 is received in tracks 28, the received portion may be accessed, but movement of the claw is constrained to translation along the length of the tracks. Other cross-sectional shapes providing similar access and constraint are used in other arrangements of body 22. In a specific example, tracks with circular or partially circular cross-sectional shapes could permit claws with received portions of matching circular or partially circular cross-sectional shapes to rotate about an axis extending along the length of the length of the track in addition to translating along that axis before being immobilized, such as by tightening of a set screw such as set screw 60 of FIG. 4, which will be discussed below.

Figure 3A:
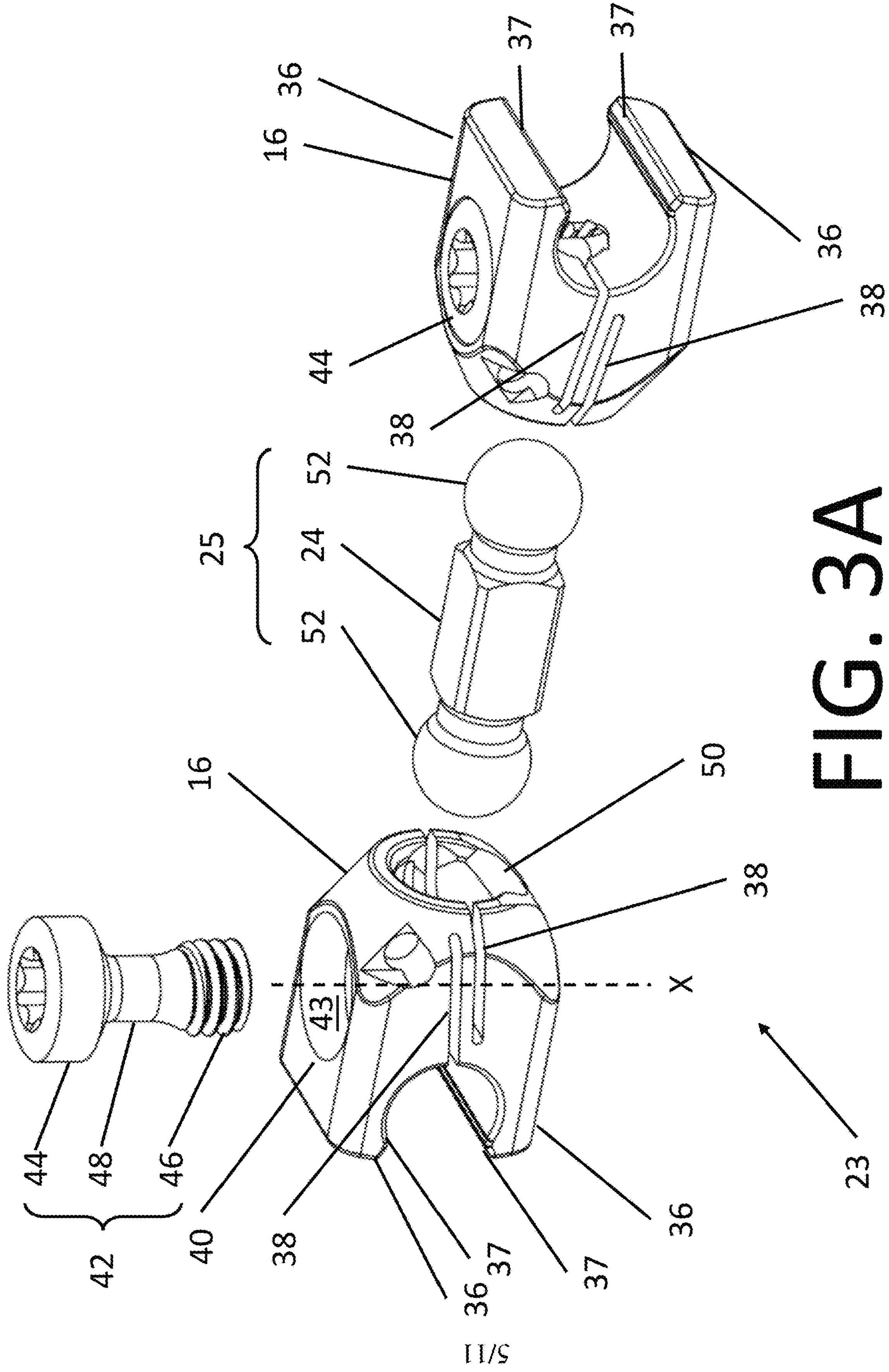
FIG. 3A is an exploded illustration of a rod clamp array of the clamp device of FIG. 1A.
Figure 3B:
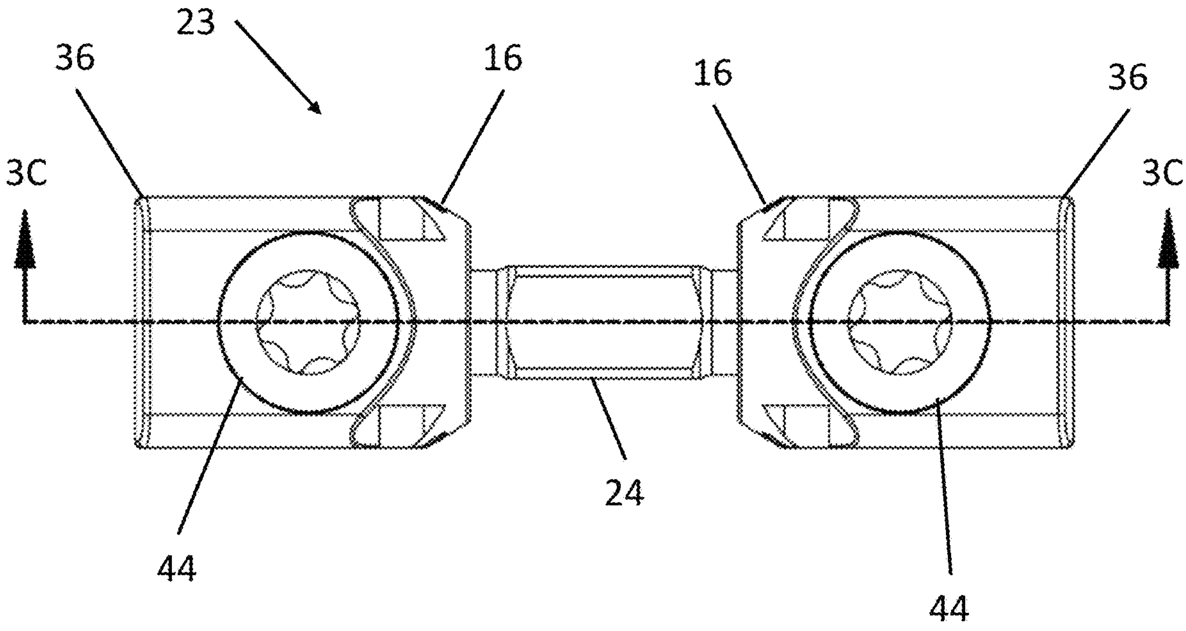
FIG. 3B is a top plan view of the rod clamp array of FIG. 3A.
Figure 3C:
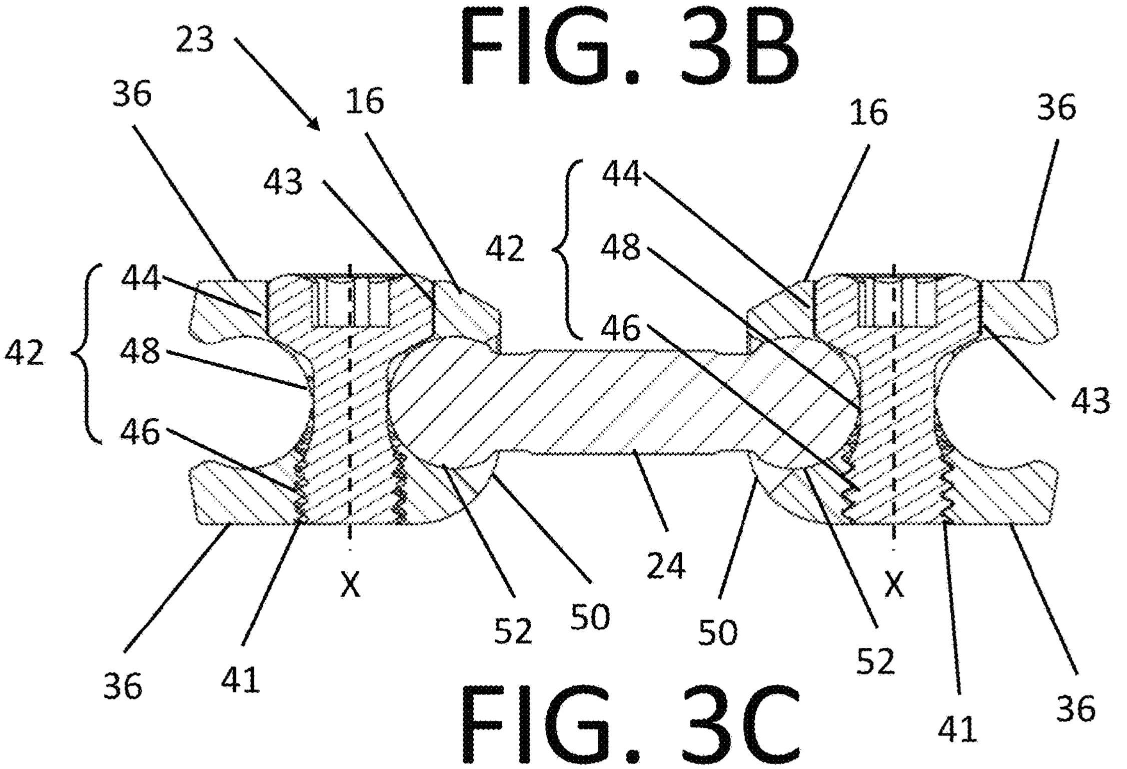
FIG. 3C is a view along section 3C-3C of FIG. 3B.

FIGS. 3A-3C illustrate a removable rod clamp array 23 according to an arrangement compatible with the above described features of rod clamping portion 12, though the above described features of the rod clamping portion 12 could be implemented with structures that differ from the illustrated example.

Rod clamp array 23 includes dumbbell 25 to which rod clamps 16 are pivotably couplable. Dumbbell 25 includes a bar 24 with a ball 52 at either end. Rod clamps 16 each include a socket 50 for closely receiving either ball 52 to provide the pivotable connection between the rod clamps 16 and dumbbell 25 as a ball-and-socket joint. In various other arrangements, rod clamps 16 may be otherwise pivotably couplable to dumbbell 25, and the dumbbell may be configured to have pivotable connection points for only one or for three or more rod clamps 16. This is important because patient anatomy often dictates that spinal rods will not line up perfectly with coupling elements or clamps. Hence, polyaxial pedicle screws are the industry standard, with rod clamps 16 essentially mimicking similar movability.

Rod clamps 16 each include two opposed jaws 36, and each jaw ends in a tooth 37 extending toward the opposed jaw. Spinal rods may therefore be retained between a pair of jaws 36 behind teeth 37. It is also contemplated to provide knurling or other friction inducing surfaces within the clamps to firmly hold the spinal rods.

Rod clamps 16 are tightenable from an open state wherein socket 50 may accept or release ball 52 and wherein jaws 36 may accept or release a spinal rod to a closed state wherein pivoting of the rod clamp about the ball and movement of the spinal rod between the jaws is inhibited or prevented entirely. In the illustrated arrangement, such tightening is enabled by a flexible design of rod clamps 16. Rod clamps 16 include notches 38 extending normal, or nearly normal in the illustrated example, to a tightening axis X, which extends in the same direction as the direction in which jaws 36 are opposed. Rod clamps 16 overall are therefore compressible along compression tightening axis X. Further, each rod clamp 16 includes one notch 38 extending from a meeting point between jaws 36 generally toward an opening of socket 50 and another notch extending from the opening of the socket generally toward the meeting point between the jaws. The opposed notches 38 create a living hinge in each rod clamp 16 extending roughly along a midline thereof. Each rod clamp 16 therefore includes two body portions separated by the living hinge which may rock relative to one another about the living hinge to separate or close jaws 36 or to loosen and tighten socket 50.

Each rod clamp 16 includes a bore 40 that extends along tightening axis X for receiving a lag screw 42. Each bore 40 includes a seat 43 of relatively large diameter, which is a portion that is counterbored, countersunk, or both as shown in the illustrated example. Threads 41 are disposed at or near an end of bore 40 opposite from seat 43. Each lag screw 42 includes a head 44, a neck 48, and a threaded portion 46. Head 44 is the only portion of lag screw 42 too large in diameter to travel into any portion of bore 40 other than seat 43 when the lag screw is inserted into the bore along tightening axis X. Rod clamp 16 may therefore be tightened to the closed state by threadingly engaging threaded portion 46 of lag screw 42 to threads 41 while head 44 is received within seat 43 and turning the lag screw to pull the threads toward the seat, thus drawing the two opposed halves of the rod clamp 16 toward each other to compress notches 38 and the living hinge.

Notches 38, bore 40, and lag screw 42 are only one example of how rod clamps 16 may be locked onto barbell 25 and rods, and other types of hinges and locks may be used in their stead. For example, the two opposed portions of each rod clamp 16 that each include a jaw 36 and part of socket 50 could instead be separated by one resilient spring or a group of springs or a mechanical hinge, and the rod clamps could be tightened down with straps, ratcheting mechanisms, buckles, clasps, latches, or collars for sliding along external tapers on the rod clamps. More generally, each rod clamp 16 and its point of attachment to dumbbell 25, such as ball 52 or otherwise, may instead be of any structure known for use in coupling spinal rods to pedicle screws, including such examples as shown in U.S. Published Application No. 2020/0100816, filed on Apr. 9, 2018, U.S. Pat. No. 10,610,265, filed on Jul. 31, 2017, US Published Application No. 2018/0368889, filed on Jun. 23, 2017, U.S. Pat. No. 10,198,970, filed on Jul. 14, 2015, U.S. Pat. No. 10,064,656, filed on Feb. 12, 2016, U.S. Pat. No. 10,918, 419, filed on Apr. 1, 2015, or U.S. Pat. No. 9,393,049, filed on Aug. 27, 2012, each of which are hereby incorporated herein by reference.

Figure 4A:
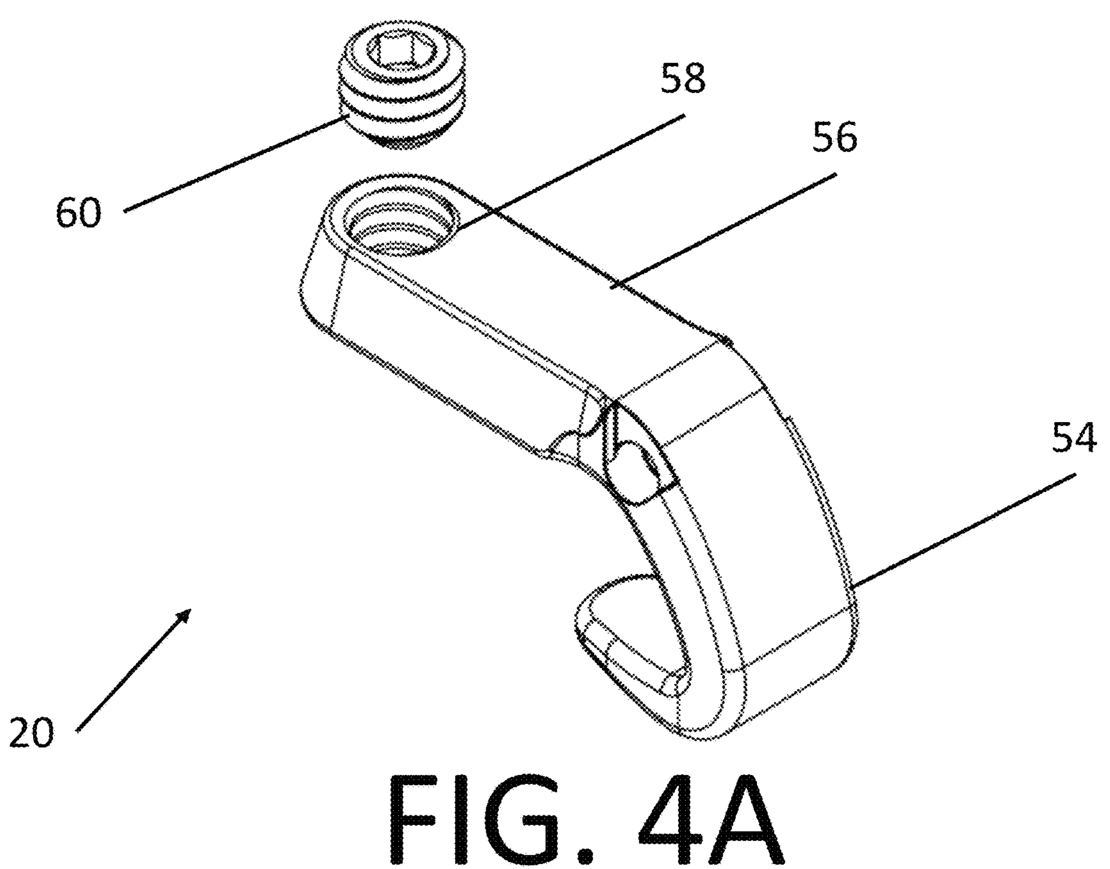
FIG. 4A is an oblique perspective view of a claw of the clamp device of FIG. 1A.
Figures 4B, 4C:
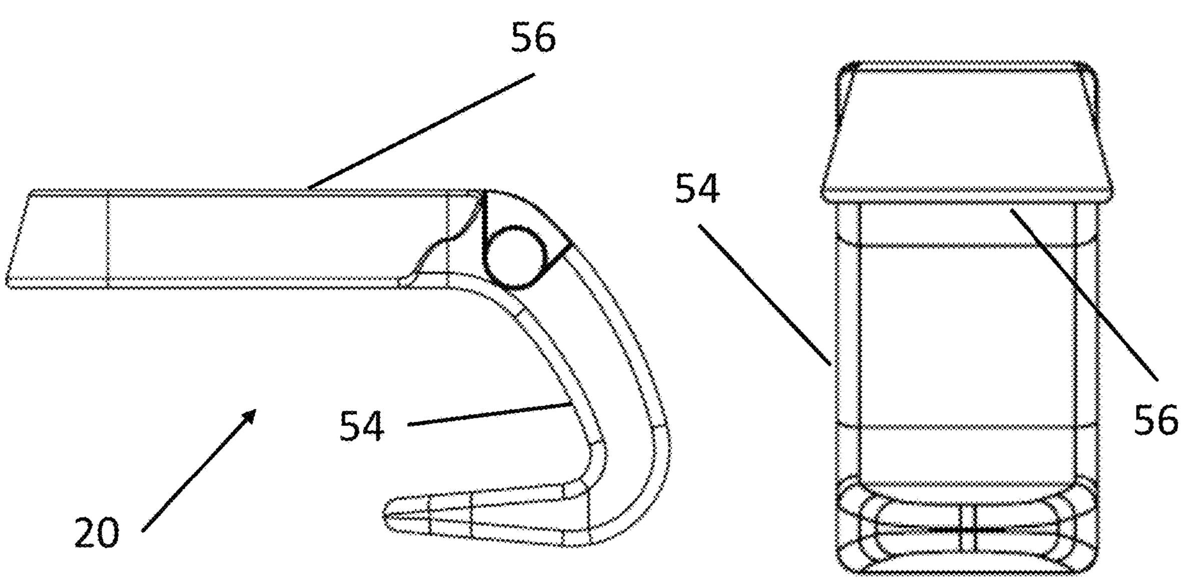
FIG. 4B is a side elevation view of the claw of FIG. 4A.
FIG. 4C is a front elevation view of the claw of FIG. 4C.

FIGS. 4A-4C illustrate claw 20 in detail. All following description of claw 20 applies equally to claw 21, which differs only in the length of tab 56 relative to its other features. Claw 20 includes hook 54, with an elongate flat tab 56 extending from one end of the hook. Tab 56 has a cross-sectional shape shown best in FIG. 4C that matches the cross-sectional shape of tracks 28 of body 22 as described above. The cross-sectional shape of tab 56 and tracks 28 of the illustrated example is trapezoidal, or at least generally trapezoidal, which provides a dovetail fit between the tab and the tracks, but the shape of the tab can vary in any of the ways noted above with regard to the tracks 28. Tab 56 of the illustrated example is therefore constrained to sliding along any track 28 when received therein, and can only exit the track by sliding out of the track's open end.

Tab 56 includes a threaded hole 58 for threadingly receiving a set screw 60. Set screw 60 may be tightened down from a top side of hole 58, from the perspective of FIGS. 4A-4C, to extend out of an opposite side of the hole and bite into body 22 at a bottom surface of a track 28 within which tab 56 is received. It is therefore possible to inhibit or prevent motion of tab 56 within track 28, and likewise inhibit or prevent motion of claw 20 relative to body 22, by tightening set screw 60 within hole 58 until the set screw bites into the body. Clamp device 10 can therefore be fixed to an object by arranging all claws 20, 21 about the object, then tightening down set screws 60 within each claw. In other arrangements, other features may be present instead of hole 58 and set screw 60 for use in immobilizing claws 20, 21 relative to body 22. For example, either the claws 20, 21 or body 22 could include a row of holes matchable to a single hole in the other of the claws and the body, and a pin could be placed through a hole of both a claw and the body to immobilize the claw. In another example, a rack-and-pinion arrangement drivable by a screw or other feature manipulatable by a surgeon could be used to advance claws 20, 21 within their respective track, and a pin could be inserted through body and any one of the rack, the pinion, or the claw itself to lock the claw in place.

Figure 5A:
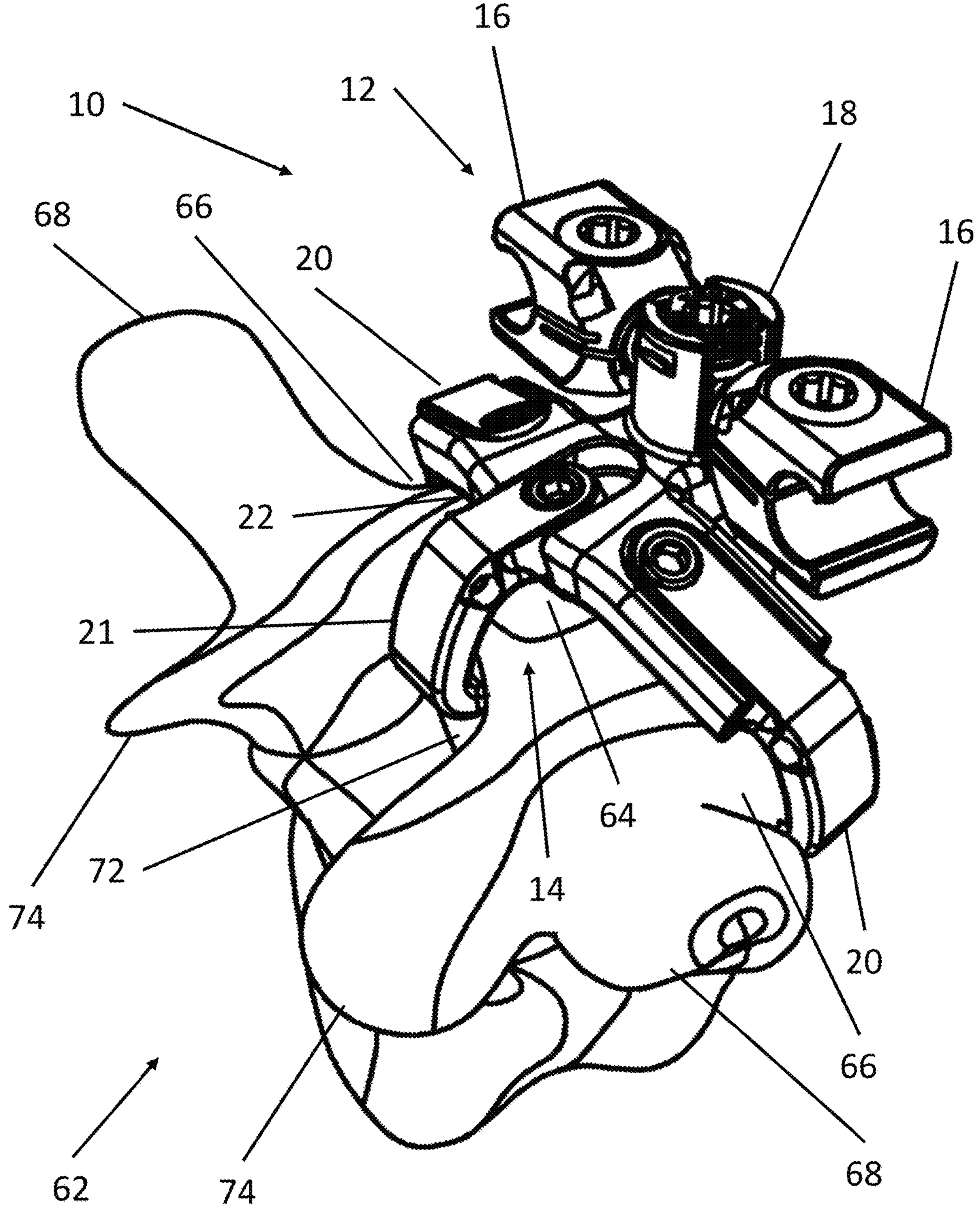
FIG. 5A is an oblique perspective view of the clamp device of FIG. 1A fixed to a vertebra.
Figures 5B, 5C:
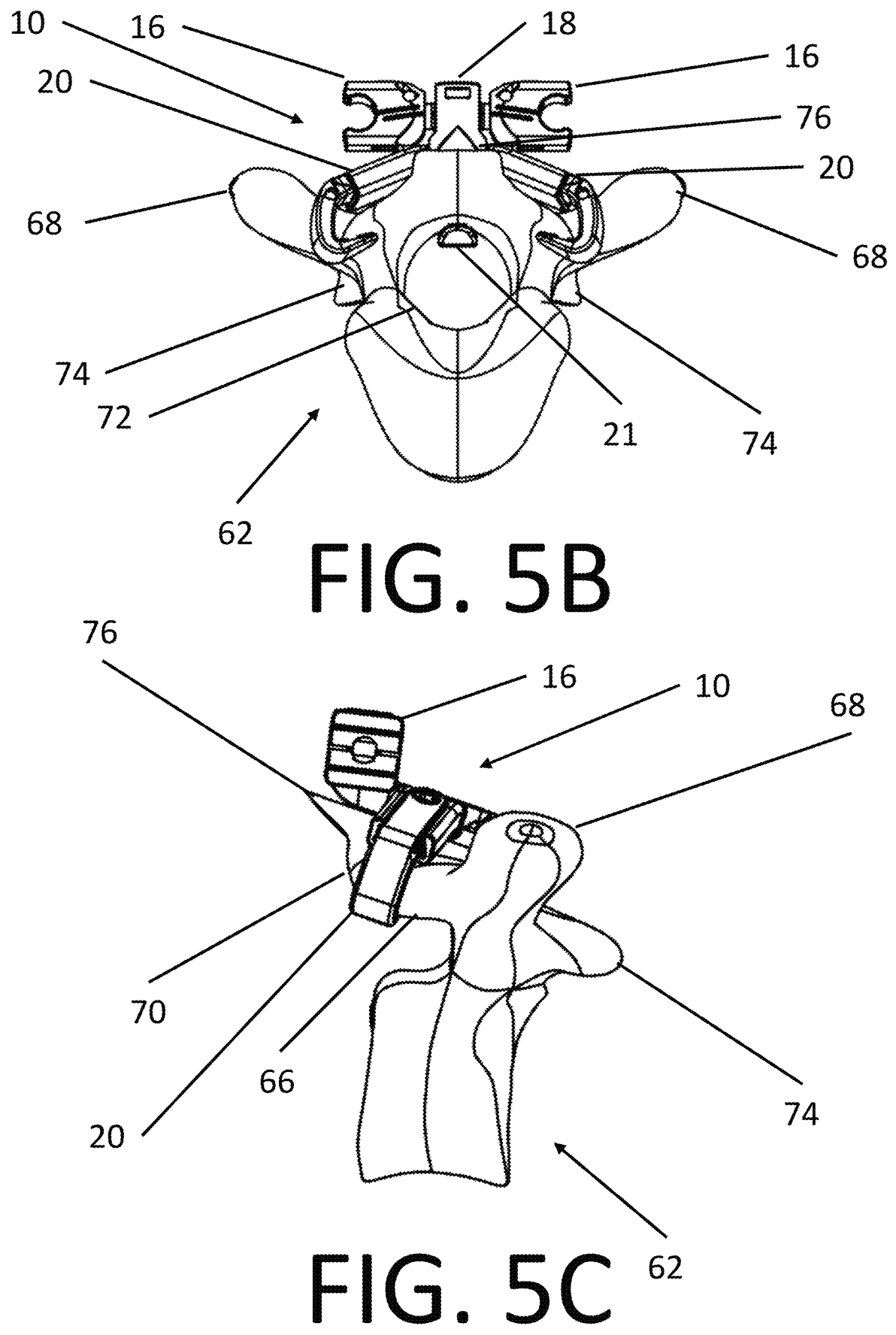

FIGS. 5A-5C illustrate an example of clamp device 10 fastened to a pars interarticularis of a vertebra 62. Body 22 is placed atop of lamina 64. Each of two claws 20, tabs 56 thereof being received within tracks 28 of the two wings 30, extend over a respective lateral edge 66 of lamina 64. Hook 54 of each claw 20 extends around and under its respective lateral edge 66 between a transverse process 68 and an inferior articular process 70. Claws 20 can be tightened onto lateral edges 66 before being secured in place relative to body 22 by their set screws 60 to prevent clamp device 10 from moving laterally, anteriorly, or posteriorly relative to vertebra 62. Similarly, claws 20 rotationally fix clamp device 10 to vertebra 62 such that turning the clamp device about the cephalad-caudad axis will also move the vertebra. Further, because clamp device 10 is positioned such that the convex angle between wings 30 faces generally in the caudad direction, claws 20 pass slightly caudad around lateral edges 66 and thereby prevent cephalad motion of the clamp device relative to vertebra 62. In other arrangements, claws 20 or wings 30 could be braced against caudad surfaces of transverse processes 68 to prevent cephalad motion of clamp device 10 relative to vertebra 62.

Vertebra 62 may be prepared before clamp device 10 is paced by removing some or all of the spinous process 76 to leave a flattened surface as shown in the illustrated example. Claw 21, the tab 56 of which is received in track 28 centered between wings 30, extends superiorly relative to the patient's anatomy. Hook 54 of claw 21 therefore hooks around and under a superior edge of the pars interarticularis between superior articular processes 74 and slightly into vertebral foramen 72. Claw 21 thereby prevents clamp device 10 from traveling in the caudad direction relative to vertebra 62 along the flattened surface of spinous process 76. Claw 21 cooperates with the anatomy of vertebra 62, particularly lamina 64 and spinous process 76 in the illustrated arrangement, to rotationally couple clamp device 10 about the lateral axis as well. As such, when clamp device 10 is clamped to vertebra 62 as shown, rotating the clamp device about the lateral axis will also rotate the vertebra. Depending on a size and intended placement of clamp devices 10 of alternative examples, flattening of spinous process 76 may be unnecessary. In such alternatives, it may be possible to brace clamp device 10 against a superior side of spinous process 76, in which case claw 21 may be unnecessary.

The above described constraint of claws 20, 21 and clamp device 10 overall to vertebra 62 also rotationally couples the clamp device to the vertebra about the anterior-posterior axis. Clamp device 10 is therefore fixed to vertebra 62 with respect to all six degrees of motion, meaning the clamp device can be manipulated in any direction to correct the position of the vertebra. As such, clamp device 10 enables any correction methods known to be performable by coupling spinal rods to pedicle screws, but without the need for driving any fasteners into vertebra 62. Example spinal rods and correction methods for which clamp device 10 may be used may be found in international application No. PCT/US2021/30618, filed May 4, 2021, the entirety of which is hereby incorporated by reference herein, but a wide variety of rods and methods otherwise implemented with pedicle screws exist and may instead be implemented with the clamp device of the present disclosure. The modular nature of clamp device 10 enables certain parts to be repositioned or swapped out for alternatives as necessary to account for differences between patients, individual vertebrae, necessary corrections, and surgeon preference. Thus, using clamp devices 10 according to the present disclosure may include, before or after initial placement of body 22, selecting either or both appropriate claws and an appropriate bar from a kit including either or both of claws of different shapes and sizes and bars of differing shapes and sizes or having differing numbers of connection points for rod clamps 16. For example, the surgeon may select the claws, connect clamp device 10 to the vertebra, then select a bar and connect the bar to body 22 of the clamp device.

Figure 6:
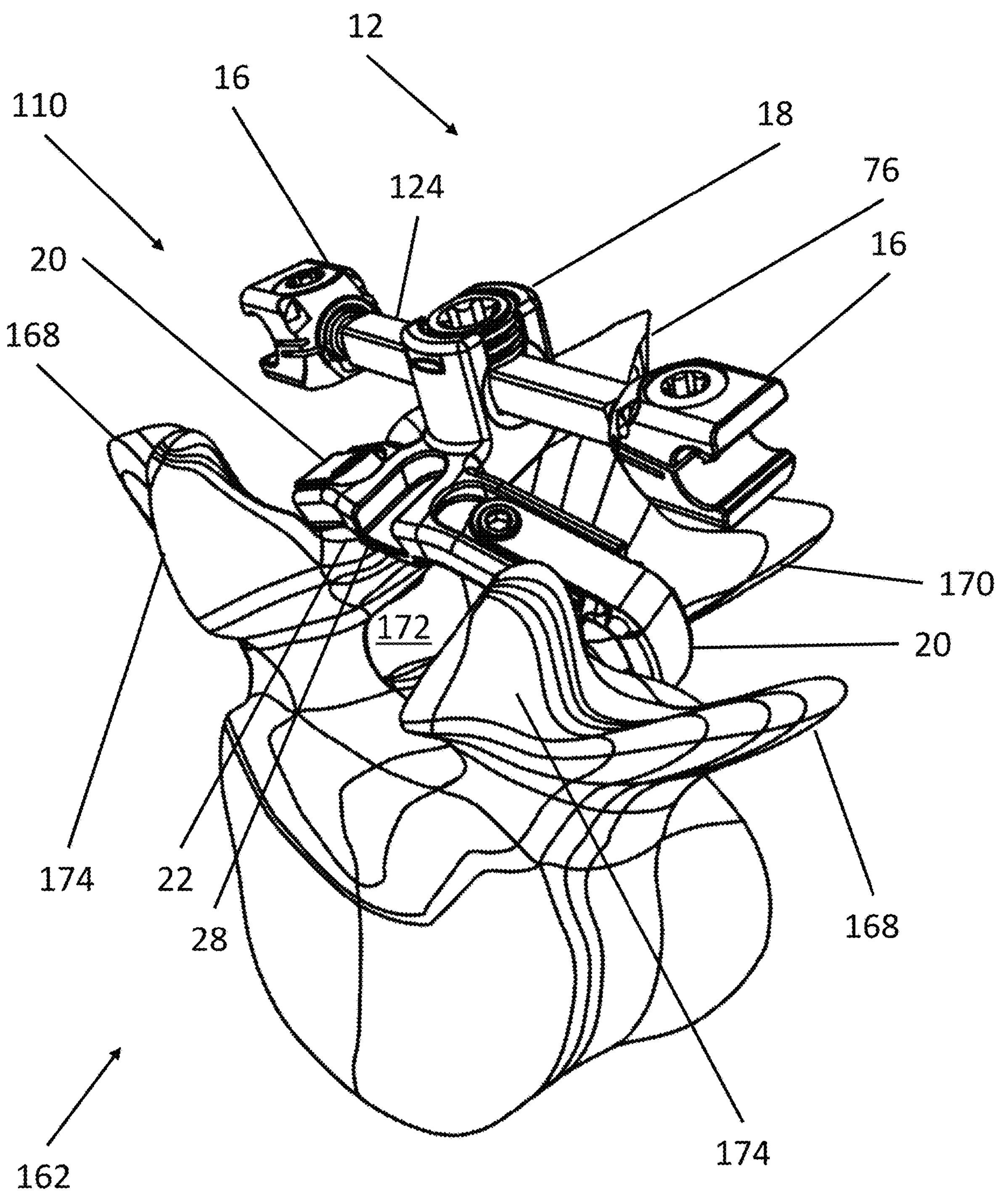
FIG. 6 is an oblique perspective view of a clamp device according to another arrangement fixed to a vertebra.

FIG. 6 illustrates a differently configured clamp device 110 clamped to a different vertebra 162. Vertebra 162 has relatively pronounced inferior articular processes 170 such as may be found in lumbar vertebrae, whereas vertebra 62 was more typical of thoracic vertebrae. Claws 20 are therefore able to fix clamp device 110 in all directions relative to vertebra 162 by hooking into the distinct notch formed between inferior articular processes 170 and transverse processes 168. Clamp device 110 is therefore sufficiently secured to vertebra 162 without any claw, such as claw 21, between superior articular processes 174 into vertebral foramen 172.

Clamp device 110 thus does not include claw 21, or any claw within the track 28 centered between the wings 30. Clamp device 110 also differs from clamp device 10 as shown in FIGS. 1A, 1B, and 5A-5C in that it includes a much longer bar 124. Bar 124 is longer to match the greater width of the pedicles of vertebra 162 relative to vertebra 62. By enabling the use of either bar 24, 124, the modularity of clamp device 10, 110 also enables a surgeon to use the clamp device to recreate the same leverage and attachment points that would be provided by driving pedicle screws into any given vertebrae by varying the distance by which rod clamps 16 are separated.

Figure 7:
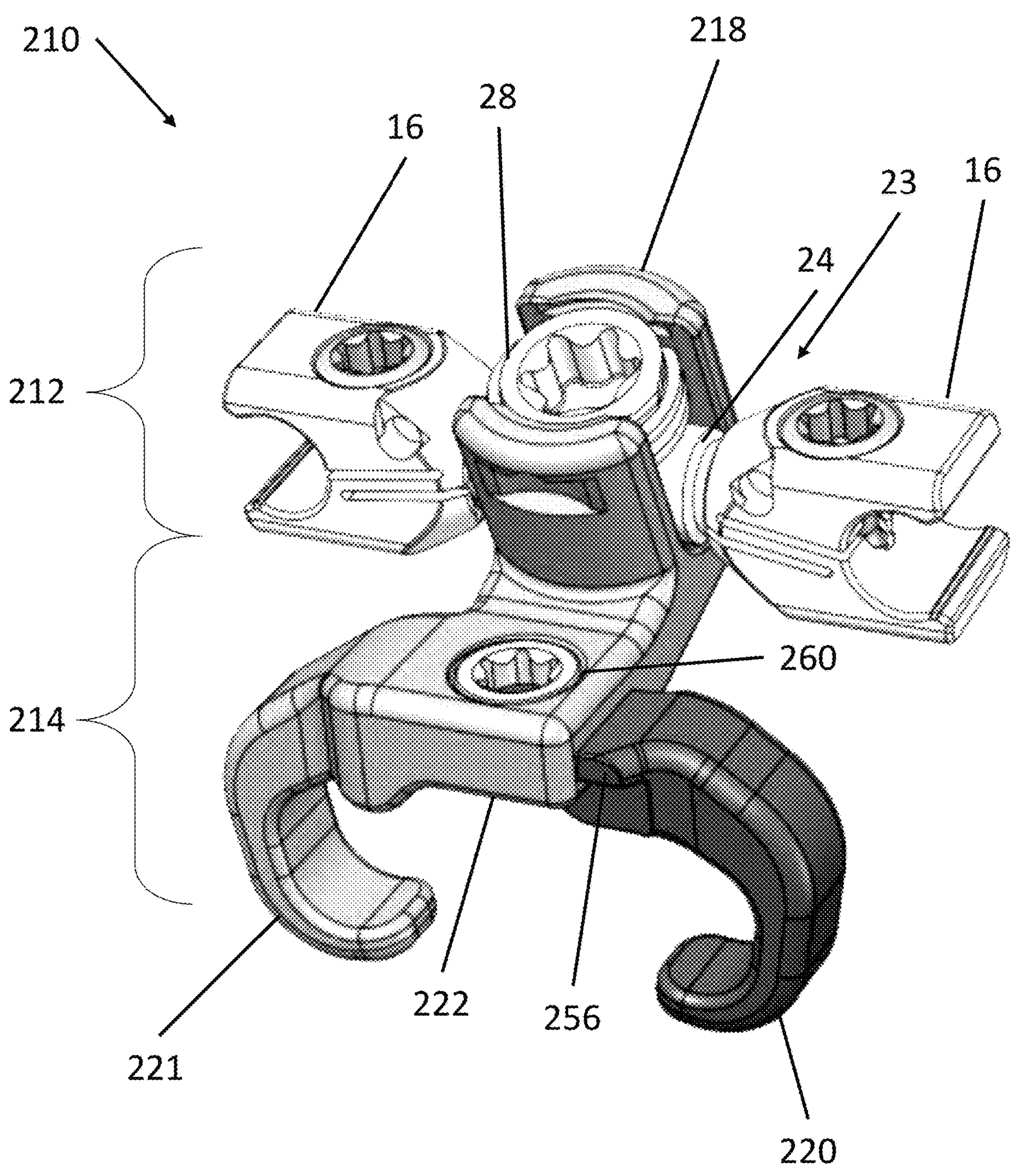
FIG. 7 is an oblique perspective view of a clamp device according to yet another arrangement.

FIG. 7 illustrates a clamp device 210 according to an alternative arrangement. In FIG. 7, like numerals refer to like elements with differences only as illustrated or described. For example, body 222 is similar to body 22 except for the distinctions shown in FIG. 7 or specifically stated below, and all variations to body 22 mentioned above could also be made to body 222.

Clamp device 210 is compatible with the same rod clamp arrays 23 as clamp device 10 described above. Rod clamping portion 212 of clamp device 210 includes a tulip 218, bar 24, two rod clamps 16 pivotably connected at either end of bar 24, and set screw 28 retaining the bar within the tulip.

Pars clamping portion 214 includes a movable claw 220 and a fixed claw 221. Movable claw 220 includes an elongate tab received within a track extending within body 222, generally similar to tracks 28 and tabs 56 of FIGS. 1A-2D and 4A-4C. However, body 222 includes a bore that threadingly receives set screw 260 and opens into the track. Movable claw 220 can be immobilized relative to body 222 by tightening the set screw to bite into the tab of movable claw 220, in contrast to tightening a set screw received in the tab to bite into the body. However, this aspect is interchangeable. That is, movable claw 220 could be replaced with claws 20, 21 and set screw 60 as described above if body 222 were reconfigured to have a corresponding track, and any or all of tracks 28 of body 22 could be reconfigured to accept claw 220 and set screw 260.

Fixed claw 221 is integrally formed with body 222. Thus, clamp device 210 could be clamped on to suitable vertebrae in a manner generally similar to those illustrated in FIGS. 5A-6 by placing body 222 onto a pars interarticularis, moving movable claw 220 such that the movable claw and fixed claw 221 hook tightly around opposed lateral edges of the lamina, and then tightening down set screw 260 to immobilize the movable claw relative to the body.

Any of the components of the above described clamp devices 10, 110, 210, including bodies, claws, rod clamps, and dumbbells, may be constructed from any sufficiently strong biocompatible material, such as, for example, stainless steel, titanium, nitinol, rigid plastics such as polycarbonate or glass filled polycarbonate, or any other suitable materials. Set screws 60, 260 may be constructed from harder material than the component the set screws are arranged to bite into, such as body 22, 222 or hooks 20, 21, 220 in various arrangements.

As noted above, the components of clamp devices 10, 110, 210 are generally modular and interchangeable, and may therefore be provided in kits such that a surgeon may select a group of components according to preference and the needs of a given procedure. The surgeon may, for example, select a body from among an assortment within the kit that may include either or both of body 22 and body 222 and other similar bodies in addition or instead. The kit may also include an assortment of claws 20, 21, 220, or similar, compatible with some or all of the bodies having tabs and hooks of various lengths or proportions that the surgeon may select from. The kit may yet further include an assortment of dumbbells 25 or clamp arrays including dumbbells 25 of various lengths, and possibly including varying numbers of attachment points for rod clamps so that the surgeon may select an appropriate dumbbell or rod array before or after claws are used to connect the selected body to a given vertebra.

Although the concepts herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A clamp device for securing at least one spinal rod to a vertebra, the device comprising:

a body including a first wing having a first track extending within and along the first wing, a second wing having a second track extending within and along the second wing, the first wing and second wing extending generally away from one another, a tulip having opposed sidewalls and an open upper end;

a rod clamp array supported by the body for releasably retaining a spinal rod, the rod clamp array including, a unitary bar releasably connected to the tulip, and two pivotably connected rod clamps supported by the unitary bar;

a first claw that is movably connected to the body, the first claw including a hook and a elongated tab extending from the end of the hook and received in the first track and that may also be received in the second track; and a second claw that is either connected to the body or integrally formed with the body.

2. The clamp device of claim 1, wherein each rod clamp is connected to the bar by a ball and socket joint.

3. The clamp device of claim 1, comprising a third claw that is movably connected to the body and wherein the first claw and third claw are removable from the body.

4. The clamp device of claim 3, wherein the third claw is different in size than the first claw and the second claw.

5. The clamp device of claim 1, wherein the tab includes a threaded hole extending therethrough, and the clamp device includes a set screw that may be driven through the hole to bear on a surface of the first track.

6. The clamp device of claim 1, wherein the body includes a threaded hole extending through a portion of the body to open into the first track and the clamp device includes a set screw that may be driven through the hole to extend into the first track.

7. The clamp device of claim 1, wherein the tab and the track create a dovetail connection to one another when the tab is received in the first track.

8. The clamp device of claim 1, wherein a third track that may also receive the tab extends within the body at a location centered between the wings.

9. The clamp device of claim 1, wherein each rod clamp in the array of rod clamps includes two jaws that meet at a living hinge provided by notches extending into the rod clamp from opposite sides of the rod clamp.

10. The clamp device of claim 9, comprising a lag screw for each rod clamp in the array of rod clamps that includes a threaded portion and a head of larger diameter than the threaded portion at an opposite end of the lag screw from the threaded potion; and wherein each rod clamp in the array of rod clamps includes a bore and threads within the bore for threadingly engaging the threaded portion of the lag screw, the bore extending across the living hinge and having both an open end and a portion too small in diameter to accept the head of the lag screw on an opposite side of the living hinge from the threads of the rod clamp.

* * * * *